United States Patent
Brunelle et al.

(10) Patent No.: US 8,070,669 B2
(45) Date of Patent: Dec. 6, 2011

(54) WALL INTEGRATED MULTISENSORY THERAPY DEVICE (75) Inventors: Henry Brunelle, Cap-Rouge (CA); Louis Gendreau, Ste-Marie-de-Beauce (CA); Stéphane Baron, Charny (CA); Pascale Vaillancourt, Saint Romuald (CA)

(73) Assignee: Gestion Ultra International Inc., St-Nicolas, Quebec (CA)

( * ) Notice: Subject to any disclaimer, the term of this patent is extended or adjusted under 35 U.S.C. 154(b) by 784 days.

(21) Appl. No.: 12/185,163

(22) Filed: Aug. 4, 2008

(65) Prior Publication Data
US 2010/0030013 A1 Feb. 4, 2010

(51) Int. Cl.
*A61M 21/00* (2006.01)

(52) U.S. Cl. ............... 600/27; 600/26; 607/85
(58) Field of Classification Search ............ 600/21–27; 128/898; 607/85
See application file for complete search history.

(56) References Cited

U.S. PATENT DOCUMENTS

| | | | |
|---|---|---|---|
| 4,640,266 A | 2/1987 | Levy | |
| 5,304,112 A | 4/1994 | Mrklas et al. | |
| 5,725,472 A * | 3/1998 | Weathers | 600/21 |
| 6,681,417 B2 | 1/2004 | Brunelle et al. | |
| 6,702,767 B1 | 3/2004 | Douglas et al. | |
| 2005/0124851 A1* | 6/2005 | Patton et al. | 600/26 |
| 2008/0004677 A1* | 1/2008 | Gay | 607/85 |
| 2008/0124509 A1* | 5/2008 | Boise | 428/45 |

FOREIGN PATENT DOCUMENTS
EP 1 946 790 A1 7/2008
* cited by examiner

*Primary Examiner* — Henry M Johnson, III
*Assistant Examiner* — Jeffrey Lipitz
(74) *Attorney, Agent, or Firm* — Norton Rose OR LLP (57) ABSTRACT

A wall integrable multisensory therapy device for securement in a wall of a room dedicated for physiological therapeutic treatment is described. The device has a convection conduit with a bottom air intake and a top air outlet. A blower is secured between the inlet port and outlet port to heat air convected therethrough. Associated with the convection conduit is a front panel incorporating therein audio speakers and two different light sources, one being a white light source and the other being a colored light source. The white light source provides a luminotherapeutic sensation and the colored light source provides a chromotherapeutic sensation. The heated air provides a thermotherapeutic sensation. An aromatic liquid dispenser is also associated with the front panel provides an aromatherapeutic sensation. An audio transmitter equipped with speakers provides for a relaxing sensation of hearing to a user person. A control module is associated with a data processor which is programmed to generate combinations of these treatments some being adjustable in intensity levels and all having time adjustment capabilities, as programmed for selection by the user person.

8 Claims, 6 Drawing Sheets

WALL INTEGRATED MULTISENSORY THERAPY DEVICE

TECHNICAL FIELD

The present invention relates to a multisensory therapy device which is integrable in a wall of a room which is dedicated for physiological therapeutic treatment.

BACKGROUND ART

Various multisensory therapy devices are known to provide a relaxed environment to relieve stress in a person. One example of such a device is described in U.S. Pat. No. 6,702, 767 wherein a housing is integrated with a chair in which a user person sits in a comfortable posture and is subjected to physiological therapeutic treatment such as audio sounds and video images which may be synchronized to an aromatic sensory component or other sensation producing devices to provide a distracting and relaxing environment to the user person. However, these devices are quite expensive, can be used by only a single person at one time and they generate a fixed and repetitive treatment. The treatment cannot be modified by the user person to provide different relaxation sessions. In order to modify the treatment, a second person, usually a technician, is required to operate a computer device. This second person also monitors the patient undergoing the sensory treatment and evaluates the patient and intervenes in the control of the sensory systems depending upon signals received from the components of the system. Accordingly, a profile of a patient being treated can be developed and stored in the computer. Such expensive systems are therefore adapted for use in clinics only for providing treatment and therapy to patients.

It would therefore be beneficial to provide a device which could be incorporated into a room of a home for personal use and which can provide a multitude of such beneficial physiological sensory treatments. For example, U.S. Pat. No. 5,304,112 describes an integrated stress reduction system which provides relaxing visual, sound, tactile and environmental effects to aid a user person in reducing his or her stress level. Again, in this system the stress level of the user person needs to be detected and a computer controls the intensity and duration of the relaxing effects. The system uses light pattern stress level display using a laser. The use of a laser adds to the complexity and high cost of such system and it is therefore only affordable to a very limited number of people. The apparatus also uses a large video device having a screen and which occupies a very large space. The laser beam is projected on the screen to form a pattern on the screen and speakers need to be mounted in the room at different locations as well as a video camera. It can therefore be concluded that this system is a biofeedback system which cannot be said to be readily available to the general public due to the expensive aspect thereof. Further, it occupies a large space and a special room needs to be built to accommodate such a system.

SUMMARY OF THE INVENTION

It is therefore a feature of the present invention to provide a multisensory therapy device which can be integrated in a wall of a room to be dedicated for physiological therapeutic treatment and wherein such a room may be a bathroom or any small enclosure wherein a thermotherapeutic air treatment can be generated and maintained by the therapy device to provide the user person the beneficial effect of heat to relieve stress. Because people frequently fail to take time to relax after a day at work or after a strenuous sport activity there is a need to provide an inexpensive multisensory therapy device which can be easily incorporated in a wall of a room of a home and which room can be customized by the user person. The system can also be used without the assistance of another person.

It is well known that stress can be reduced by physiological therapeutic treatment capable of being sensed by a user person and the therapy device of the present invention provides a unit which can deliver a plurality of sensory treatments in a programmable sequence.

Another feature of the present invention is to provide a wall integrable multisensory therapy device which utilizes five sensory treatments including a thermotherapeutic air treatment, a luminotherapeutic treatment, a chromotherapeutic treatment, an audio treatment to generate a sensation to the hearing and an aromatherapeutic stimulating sensation treatment.

Another feature of the present invention is to provide a wall integrable multisensory therapy device which can be incorporated in a wall of a room between adjacent existing studs in such wall thereby making the system easy to install while not occupying the floor space of a room.

Another feature of the present invention is to provide a wall integrable multisensory therapy device which has a programmable data processor capable of programming combinations of treatments using two or more of the available sensory therapies and wherein the treatments have variable intensity levels and time duration adjustment capabilities which are selected by the user person by simple switch selection or which may be configured by the user person.

Another feature of the present invention is to provide a wall integrable multisensory therapy device which is easy to service and uses interchangeable replacement parts and which is aesthetically pleasing.

Another feature of the present invention is to provide a wall integrable multisensory therapy device which can be incorporated in a bathroom and in a wall adjacent a shower area or a bathing area and which is visible to the user person while using the shower or bathing area.

According to the above features, from a broad aspect, the present invention provides a wall integrable multisensory therapy device for securement in a wall of a room to provide for physiological therapeutic treatment. The device comprises an air convection conduit having a bottom air intake port and an upper air outlet port. A blower is provided in the conduit for displacing air from the air intake port to the air outlet port. Air heating means is secured in the conduit intermediate the air intake port and the air outlet port for producing a thermotherapeutic air treatment to generate a sensation of touch to a user person. Sound generating speaker means is provided in the front panel of the device to generate an audible sensation to the user person. The front panel co-extends with the air convection conduit and permits access to an interior space of the convection conduit. A first light source is provided for producing a luminotherapeutic treatment in a frontal area of the front panel to generate a visual sensation to the user person. A second lighting source generates a chromotherapeutic treatment in the frontal area of the front panel to generate a further and different visual sensation to the user person. Aromatic liquid dispensing means dispenses an aromatic substance in the air displaced in said conduit to produce an aromatherapeutic treatment thereby stimulating a sensation of smell to the user person. A control module is associated with a programmable data processor which is programmed to generate sensation stimulus from combinations of at least two of the treatments. The treatments have variable intensity levels and time duration adjustment capabilities. The control module has switch means to select a desired one of the programmed sensation stimulus.

BRIEF DESCRIPTION OF THE DRAWINGS

A preferred embodiment of the present invention will now be described with reference to the accompanying drawings in which.

DESCRIPTION OF PREFERRED EMBODIMENTS

Referring now to the drawings and more particularly to FIGS. 1 to 4 there is shown generally at 10 the wall integrable multisensory therapy device of the present invention. The device consists essentially of an air convection conduit 11, as better shown in FIG. 2, which is provided with a bottom air intake port 12 and an upper air outlet port 13. A blower 14 is mounted in the conduit at the outlet for displacing air from the air intake port 12, adjacent a floor area, to the air outlet port 13 elevated from the floor. As herein shown, the blower 14 is located in the air outlet port 13 to provide easy access thereto through this air intake port for installation and future maintenance, if necessary.

Figure 2:
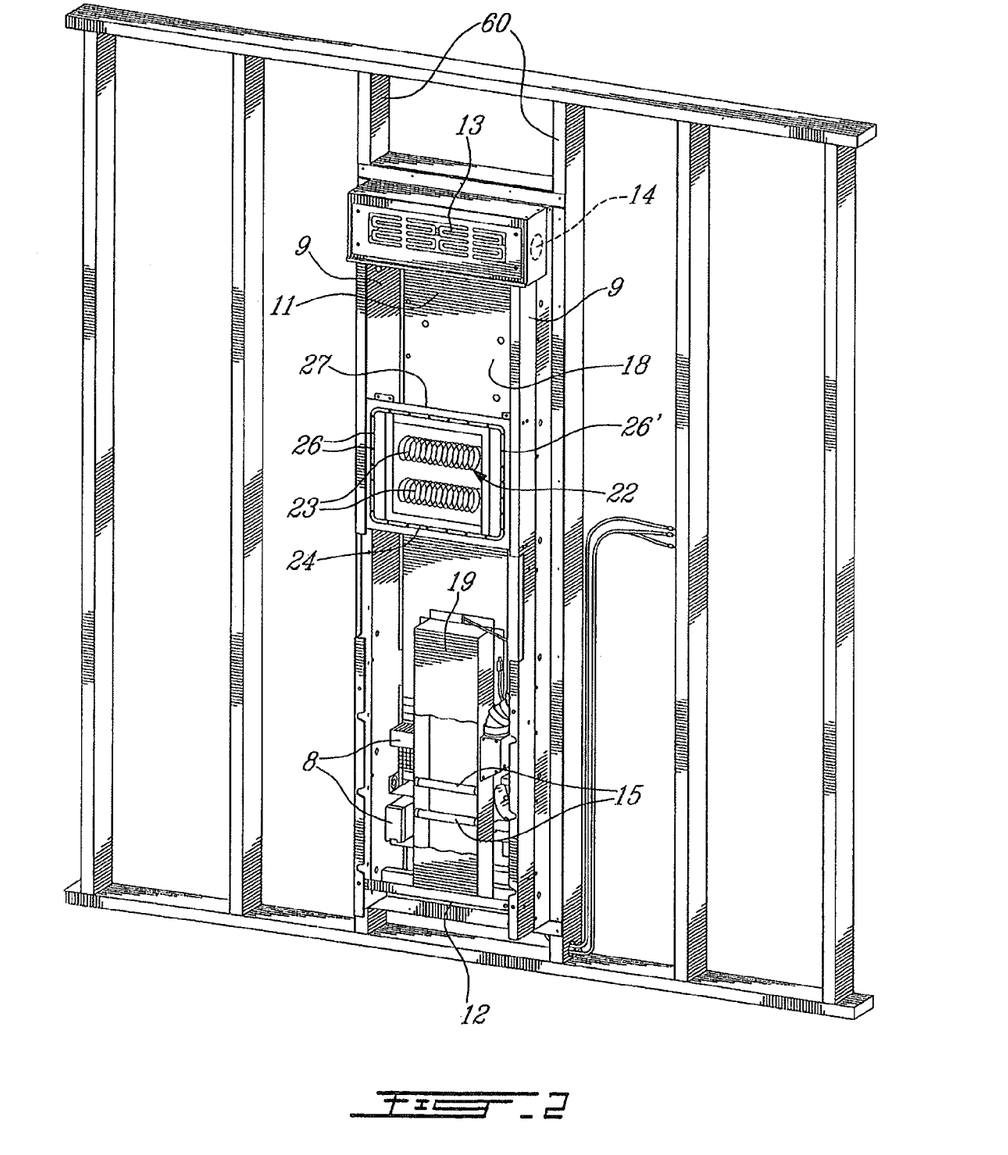
FIG. 2 is a perspective showing the mounting frame with some accessories mounted between opposed studs in a wall of a room to be used for multisensory therapeutic treatments.

As better shown in FIG. 2, resistive heating elements 15, which constitute air heating means, are secured in the air convection conduit 11 intermediate the air intake port 12 and the air outlet port 13 for heating the air convected therethrough to thereby provide a thermotherapeutic air treatment to a person in a room or enclosure sitting or standing at a desired location in proximity to the therapy device 10 to impart a sensation of "feel" to the skin of a user person.

As shown in FIGS. 1 to 4, a front panel 16 is secured to the frame 9 spaced forwardly of the air convection conduit 11 in a frontal upper area thereof by a suitable hinge 17, adjacent a large opening 18 in front of the conduit 11, whereby to provide a space for the mounting of other sensory units described later. The heating elements 15 are herein shown protected by a protective heat reflective shroud 19 spaced in a frontal, lower area of the conduit 11. A lower hinged panel 16' conceals the shroud 19 and other hardware 8.

Figure 4:
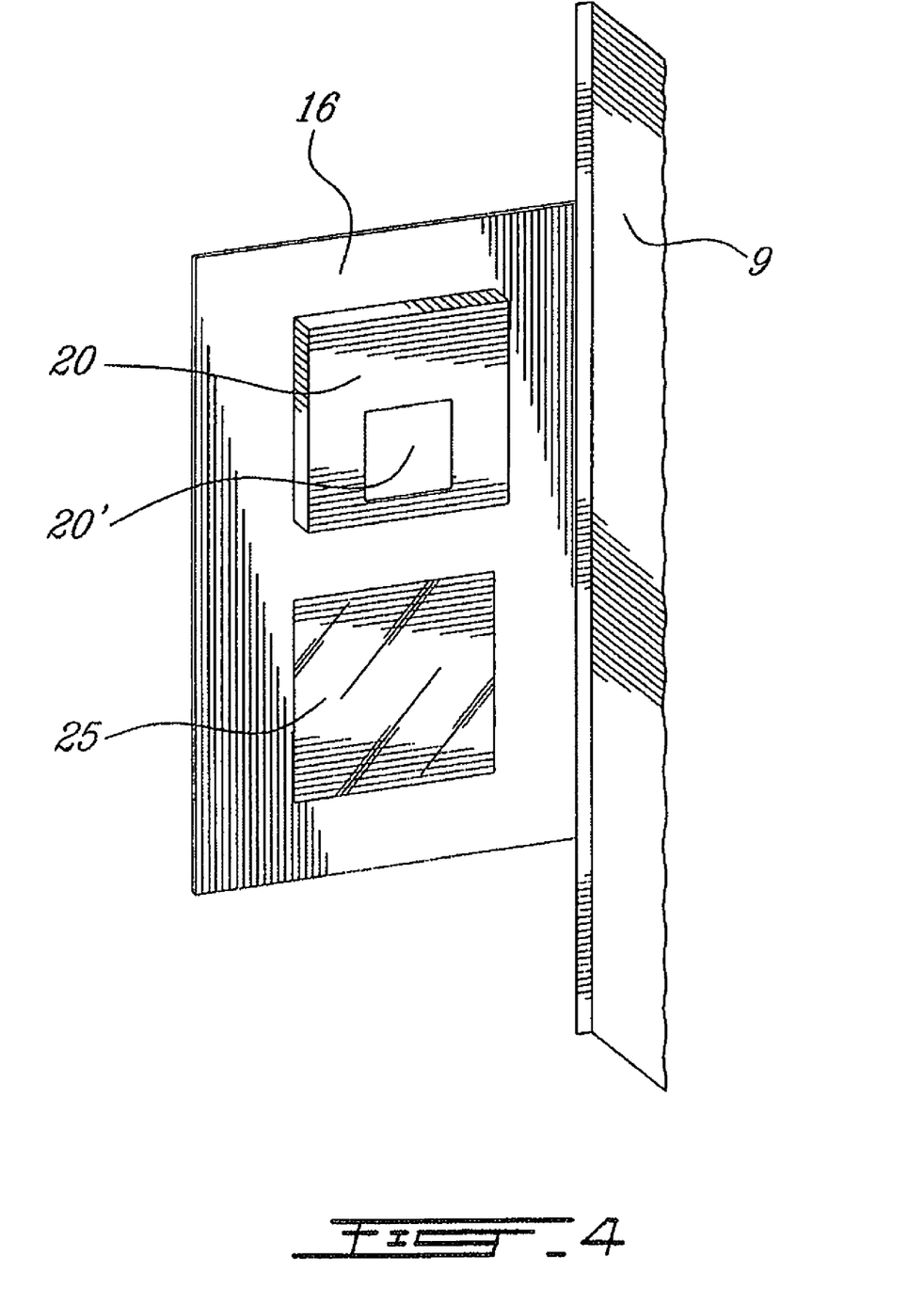
FIG. 4 is a perspective view showing the top hinged panel opened to expose some of the sensory therapeutic treatment devices.

As also better illustrated in FIG. 4, a sound speaker unit 20 is secured to the panel 16 and accessible from the rear of the front upper panel 16 and mounted behind a sound transmitting panel 21 of the front panel 16. The speaker unit 20 generates audio sounds such as music, in a frontal area of the therapy device 10 whereby to generate an audible sensation to the user person. A cassette or disc 20' is removably secured in the unit 20. A first light source 22 which is herein shown as comprised of one or more, herein a plurality of fluorescent light bulbs 23 are mounted in a waterproof housing 24 of rectangular shape, secured between the frame members 9 in an upper area of the frame. These fluorescent light bulbs or tubes 23 generate a white light intensity of about 10K to 15K of lux through a window 25 of the front upper panel 16 to illuminate the frontal area of the therapy device and impart white light on a user person to provide a luminotherapeutic treatment by immersing the user person in an environment of very bright white light.

A second light source is constituted by a plurality of different colored LED (Light Emitting Diodes) lamps 26 secured in a ribbon 26' (see FIG. 2) held in a channel (not shown) all about a flange wall 27 of the waterproof housing 24. These LED lamps generate a colored light through the window 25 which color may be a single color or variable colors depending on the programmed treatment. The colored light provides a chromotherapeutic treatment to a user person in the frontal area of the front upper panel 16 providing to the user person a further visual sensation.

With reference to FIG. 2, there is shown an aromatic liquid dispensing vaporizer unit 28 provided with a vaporizer (not shown) which dispenses an aromatic oil vapor within the convection airflow through an opening in the air convection conduit 11. Accordingly, the convected hot air can also contain an aromatherapeutic stimulus to the user person. The vaporizer unit is accessible behind the lower hinged panel 16' and accessible when the door is open to add aromatic oil therein.

Figure 1:
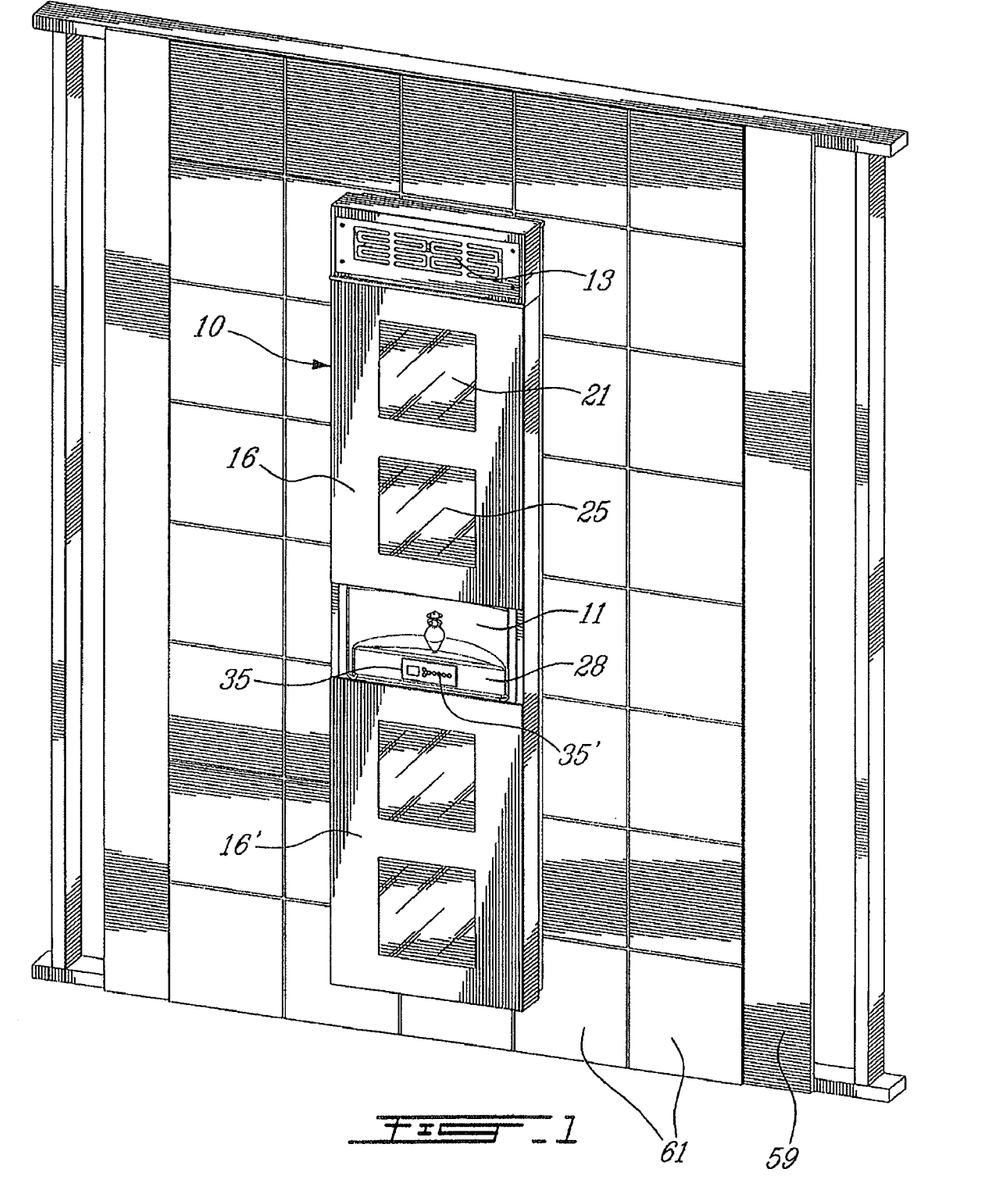
FIG. 1 is a perspective view of the wall integrated multi-sensory therapy device of the present invention with the watertight frontal hinged panels shown in an installed position.
Figure 5:
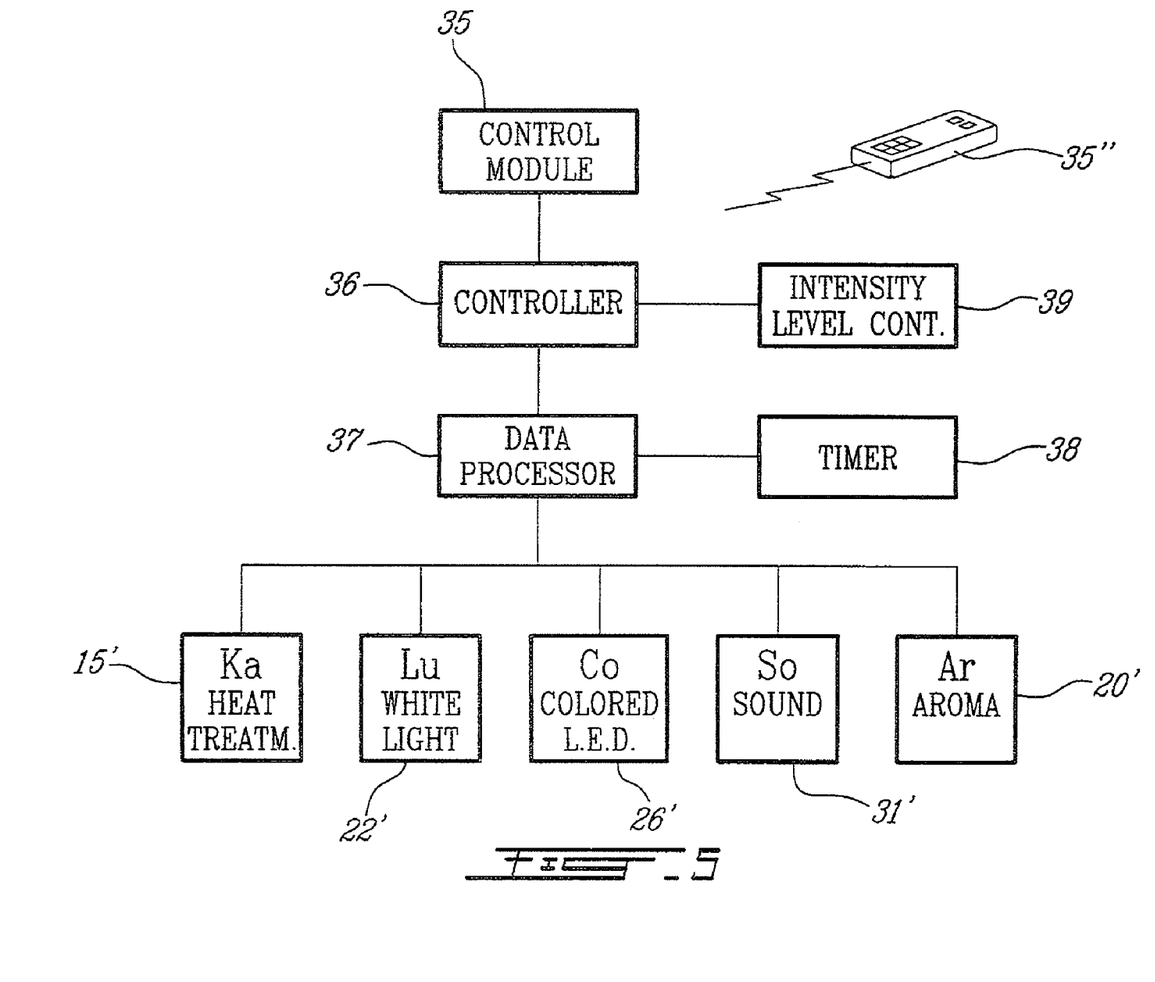
FIG. 5 is a block diagram illustrating the control system associated with the sensory therapeutic devices which are controlled by a control panel or hand held remote device interfaced with a controller and data processor.

With specific reference now to FIGS. 1 and 5 there is shown a control module 35 mounted in the top end of the lower front panel 16'. The panel 16' provides access to the control from the rear of the hinged lower front panel 16'. This control module 35 is miniaturized and has a controller 36 built therein and associated with a data processor 37 which is programmed to generate sensation stimuli from combinations of a least two of the treatments which are integrable into a programmed stimuli. Each of the treatments is herein schematically represented by reference numerals 15', 22', 26', 31' and 20' representing the five sensory stimuli of the present invention. A timer device 38 also provides for setting the time of operation of any of these sensory treatment generating devices. An intensity level adjustment control, as herein schematically depicted by block 39, also provides for the intensity level adjustment to each of the sensory treatment devices 15', 22', 26', 31' and 20' which are herein designated respectively by the symbols $K_a$, $L_u$, $C_o$, $S_o$ and $A_r$. These symbols designate respectively sensations of heat, white light environment, colored light environment, sound and aroma.

With reference now to Table A, there is illustrated the various parameters of these sensation treatment devices with the devices being identified in Column 40, their sensation in Column 41, and their availability for incorporation into a sensory treatment, that being incorporable or not in Column 42. Column 43 illustrates whether or not the sensory treatment device is adjustable and as herein shown, the heat and white light devices are not provided with adjustments as they are always constant. That is to say, the fan operates at a constant speed to assure that there is a proper convection flow to provide heated air at an adequate volume and temperature and the white light is either always on or off. However, the LED lamps which provide the chromotherapeutic treatment are adjustable in color, intensity and color combinations. The audio sound transmitter is also adjustable in intensity and may be made variable during the length of a programmed sensation stimuli treatment. The aromatic dispenser is also controllable.

It is also pointed out, although not shown herein, that graphic representations can be generated in a panel or screen (not shown but obvious to a person skilled in the art). Such a panel may be constructed of acrylic and technologies are known to project light from an edge of such panel whereby the light is transmitted by the panel to illuminate graphics etched into the panel.

TABLE A

| ELEMENT | SENSES | STATE | CHOICE | ILLUSTRATION ON THE RANGE | INTENSITY |
|---|---|---|---|---|---|
| $K_a$ | Touch | Present or absent | no | continuous line | low to high |
| $L_u$ | Sight | Present or absent | no | continuous line | low to high |
| $C_o$ | Sight | Present or absent | infinite | continuous feature according to the color of the care | low to high |
| $S_o$ | Hearing | Present or absent | infinite | graphic representation of the different sounds | low to high |
| $A_r$ | Smell and Taste | Present or absent | infinite | continuous feature and gradual reduction. Various colors according to different scents | low to high |

Table B illustrates a typical modulated sensation stimuli treatment. As herein shown in block, such a treatment would have a certain time duration and the introduction period of the treatment may have a fixed value, as shown in block, for each of the sensory treatment devices used in the treatment. After a predetermined time limit these treatment devices may become variable in intensity and time as illustrated by block and during a treatment period perhaps only one of the treatment devices would be made variable and the others fixed or the other removed from the treatment, as illustrated by block. The treatment period would then go through a further variable time period as illustrated by block and the treatment would be terminated during a fixed exit time period where all of the operational parameters of the treatment devices are fixed.

TABLE B

| SEQUENCE | INTRODUCTION | TRANSITION | TREATMENT | TRANSITION | EXIT |
|---|---|---|---|---|---|
| Time | Fixed value | Variable | Variable | Variable | Fixed value |

Table C shows a typical program function of all of the five treatment devices and their adjustable capabilities during a 30 minute sensation stimuli treatment, the details being shown in the same cycle as illustrated in Table B. The beginning of the cycle is a period of introduction 53 followed by a period of transition leading to an optimum treatment period for a predetermined time of the stimulus session and then again cycling the treatment devices through a further transition period and then to a constant exiting period as illustrated by these columns.

TABLE C

| INTRODUCTION | Mix 1 | TRANSITION | Mix 2 | TREATMENT | Mix 3 | TRANSITION | Mix 4 | EXIT |
|---|---|---|---|---|---|---|---|---|
| Fixed Progressive 10% 50% | Fixed Progressive | Variable Constant 70% | Fixed Progressive | Variable Constant 70% | Fixed Progressive | Variable Progressive 50% 30% | Variable Progressive | Fixed Constant 10% |
| Constant Blue | Skip | Constant Yellow | Skip | Constant Blue | Skip | Constant Blue | Skip | Constant Blue |
| Constant 100% | Skip | Constant 100% | Skip | Constant 100% | Skip | Constant 100% | Skip | Constant 100% |
| Constant 100% | Skip | Constant 100% | Skip | Constant 100% | Skip | Constant 100% | Skip | Constant 100% |
| File 2 | Skip | File 5 | Skip | File 8 | Skip | File 1 | Skip | File 12 |
| Constant 30% | Progressive | Progressive 40% 70% | Progressive | Constant 80% | Progressive | Constant 80% | Progressive | Progressive 70% 20% |
| Aroma 4 Constant 100% | Skip | Aroma 3 Constant 40% | Skip | Aroma 7 Progressive 70% 0% | Skip | Aroma 4 Constant 10% | Skip | Aroma 4 Constant 0% |
| 4 min. | | 2 min. | | 7 min. | | 2 min. | | 0 min. |
| Aroma 7 Constant 100% | Skip | Aroma 1 Constant 0% | Skip | Aroma 10 Progressive 30% 10% | Skip | Aroma 10 Constant 10% | Skip | Aroma 10 Constant 0% |
| 1 min. | | 0 min. | | 12 min. | | 1 min. | | 0 min. |

As shown in FIG. 1, the control module 35 is provided with touch switches 35' which are actuated by touch. It is conceivable that switches may be provided to permit the user person to modify the time duration of the programmed treatments and by modifying these time durations the computer would automatically reconfigure the various periods of the sensory treatments as programmed. A remote control device 35", as shown in FIG. 5, may also be use to command the controller 36.

Figure 3:
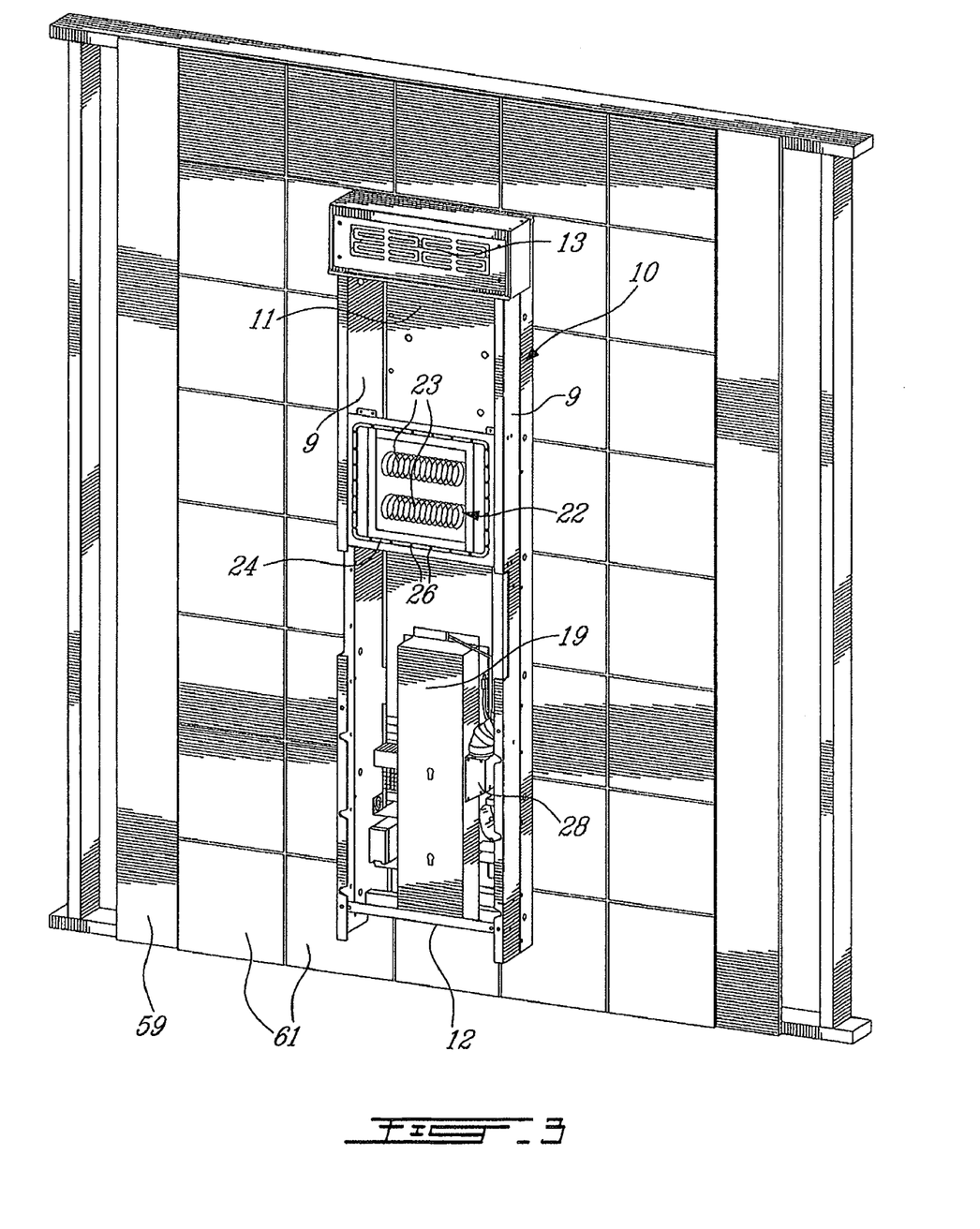
FIG. 3 is a perspective view of the wall surrounding the mounting frame having been closed by wall boards on which ceramic tiles are installed.
Figure 6:
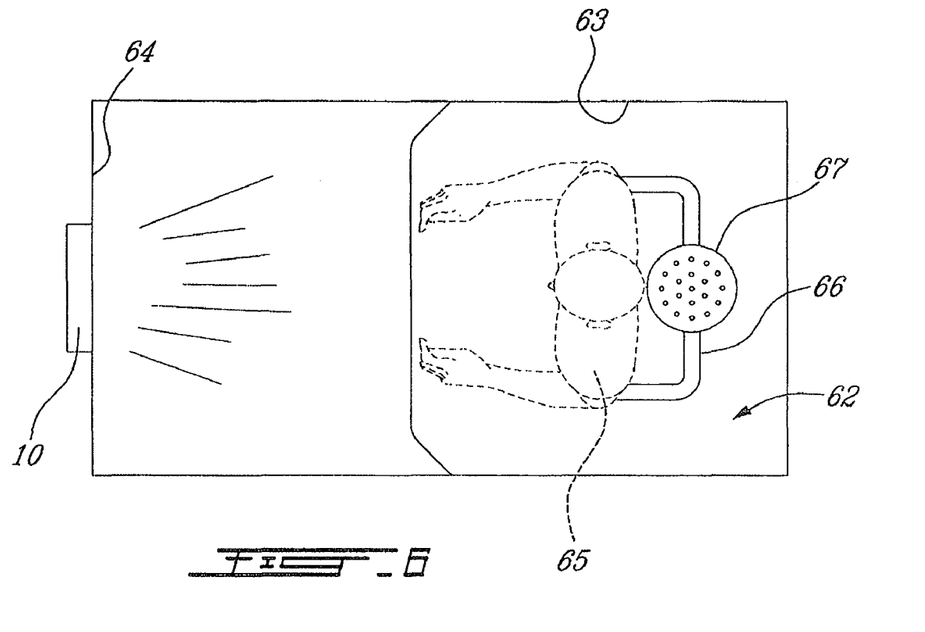
FIG. 6 is a top floor plan view of a bathroom shower area showing the therapy device of the present invention integrated into a wall facing the shower area.
Figure 7:
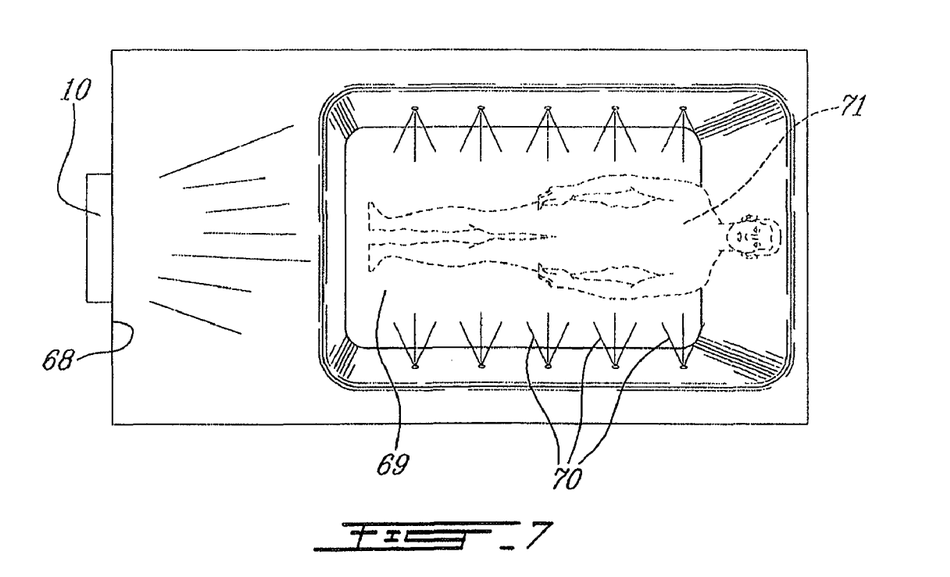
FIG. 7 is a top floor plan view similar to FIG. 8 but showing the therapy device of the present invention integrated in a wall facing a hydrotherapeutic bath tub.

As shown in FIG. 2, the therapy device 10 of the present invention can be easily incorporated in an existing wall structure of a room by opening an area in a wall between a pair of adjacent studs 60. The conduit 11 would conveniently have a width of about 16 inches which is the standard spacing between these studs 60. Because the unit would most likely be mounted in internal walls of a house these internal walls do not have insulation and provide a large open gap to accommodate the therapy device 10. Existing wiring or plumbing can also be easily reoriented to provide adequate space for the unit 10. As shown in FIGS. 1 and 3, the wall area surrounding the unit 10 is preferably covered with ceramic tiling 61 secured to back panel 59, particularly if the unit is mounted in a bathroom, as illustrated in FIGS. 6 and 7. This facilitates cleaning as condensation can accumulate about the unit due to the hot damp environment when used in a bathroom.

As shown in FIG. 6 there is shown a shower enclosure 62 mounted in an enclave 63 of a room with the therapeutic device 10 of the present invention mounted in a wall 64 facing the shower unit 62. Accordingly, a user person 65 can position himself on a chair 66 under the showerhead 67 in front of the therapy device and benefit from the sensory treatments generated by the device 10 and water flowing down on the body from the showerhead 67 during a period of treatment. The showerhead could be turned on during portions of the treatment cycle, such as during the TREATMENT period shown in Table B.

FIG. 7 illustrates a further arrangement wherein the therapy device 10 is disposed in a wall 68 facing a hydro massaging bathtub 69 which is provided with air or water jets 70 wherein the user person 71 undergoes a hydrotherapeutic treatment while further undergoing the sensory stimulus, provided by the therapy device 10 of the present invention. In such an application the chromotherapy may not be activated if one is incorporated into the bathtub 69. On the other hand, it could be used in combination with the one provided with the bathtub 69.

It is within the ambit of the present invention to cover any obvious modifications of the wall integrable multisensory therapy device of the present invention, provided such modifications fall within the scope of the appended claims. For example, it is conceivable that a video device may also be provided and interfaced with the therapy device 10 through the control module. A video program would also be selected by the user person and be synchronized with the audio or some or all of the therapeutic treatment devices provided with the therapy device 10 of the present invention. Other therapeutic treatment devices and functions can be integrated into the therapy device of the present invention.

We claim:

1. A wall integratable multisensory therapy device for securement in a wall of a room dedicated for physiological therapeutic treatment, said device comprising an air convection conduit having a bottom air intake port and an upper air outlet port, a blower in said conduit for displacing air from said air intake port to said air outlet port, air heating means secured in said conduit intermediate said air intake port and said air outlet port for producing a thermotherapeutic air treatment to generate a sensation of touch to a user, sound generating speaker means in a front panel of said device to generate an audible sensation to the user, said front panel co-extending with said air convection conduit and permitting access to an interior space of said air convection conduit, a first light source for producing a luminotherapeutic treatment in a frontal area of said front panel to generate a visual sensation to the user, a second lighting source for generating a chromotherapeutic treatment in said frontal area of said front panel to generate a further different visual sensation to the user, aromatic liquid dispensing means for dispensing an aromatic substance in the air displaced in said conduit to produce an aromatherapeutic treatment thereby stimulating a sensation of smell to the user, and a control module associated with a programmable data processor programmed to generate sensation stimulus from combinations of at least two of said treatments, said treatments having variable intensity levels and duration adjustment capabilities, said control module having switch means to select a desired one of said programmed sensation stimulus.

2. A wall integratable therapy device as claimed in claim 1 wherein said first light source is comprised of one or more fluorescent light sources capable of generating a white light intensity of about 10,000 lux.

3. A wall integratable therapy device as claimed in claim 1 wherein said sound generating speaker means are coupled to a programmable audio transmitting device.

4. A wall integratable therapy device as claimed in claim 1 wherein said front panel is an access door panel, said access door having a hinged water-tight thin transparent frontal panel hingedly secured thereover and capable of transmitting sound and light.

5. A wall integratable therapy device as claimed in claim 1 wherein said front panel is hingedly secured to said air convection conduit to provide access to an interior space of said conduit and devices secured therein.

6. A wall integratable therapy device as claimed in claim 1 wherein said aromatic liquid dispensing means is comprised of an aromatic oil contained in a droplet dispenser and having spray producing means to dispense a spray of said aromatic oil in said air convection conduit above said blower.

7. A wall integratable therapy device as claimed in claim 2 wherein said fluorescent light sources are contained in a waterproof housing secured to said conduit behind said front panel, said waterproof housing having a contour wall in which a plurality of said (light emitting diodes) are secured all around said waterproof housing.

8. A wall integratable therapy device as claimed in claim 1 wherein said switch means of said control panels provides for the user to select a predefined sensation experience which is programmed using a selected sequential order of said treatments, the time of some of said treatments and the intensity of individual ones of said treatments, said sensation experience having a time variable transition period.

* * * * *